(12) United States Patent
Wainberg et al.

(10) Patent No.: US 12,207,862 B2
(45) Date of Patent: Jan. 28, 2025

(54) DEVICE AND CARTRIDGE FOR SKIN TREATMENT

(71) Applicant: E.S.I Novel Ltd., Herzeliya Pituach (IL)

(72) Inventors: Arie Wainberg, Yokneam Ilit (IL); Gdalihu Almuznino, Migdal HaEmek (IL); Alexander Treystman, Migdal HaEmek (IL)

(73) Assignee: E.S.I Novel Ltd., Herzeliya Pituach (IL)

( * ) Notice: Subject to any disclaimer, the term of this patent is extended or adjusted under 35 U.S.C. 154(b) by 1071 days.

(21) Appl. No.: 17/042,207

(22) PCT Filed: Jan. 29, 2019

(86) PCT No.: PCT/IL2019/050114
§ 371 (c)(1),
(2) Date: Sep. 28, 2020

(87) PCT Pub. No.: WO2019/193586
PCT Pub. Date: Oct. 10, 2019

(65) Prior Publication Data
US 2021/0022797 A1  Jan. 28, 2021

Related U.S. Application Data

(60) Provisional application No. 62/755,489, filed on Nov. 4, 2018, provisional application No. 62/652,358, filed on Apr. 4, 2018.

(51) Int. Cl.
*A61B 18/14* (2006.01)
*A61B 18/00* (2006.01)

(52) U.S. Cl.
CPC ...... *A61B 18/14* (2013.01); *A61B 2018/0047* (2013.01); *A61B 2018/00613* (2013.01);
(Continued)

(58) Field of Classification Search
CPC .... A61B 2018/0047; A61B 2018/0091; A61B 2218/002; A61B 2018/00452–0047; A61B 2018/00029
See application file for complete search history.

(56) References Cited

U.S. PATENT DOCUMENTS 6,394,984 B1   5/2002  Hill
2004/0167500 A1*  8/2004  Weckwerth .......... A61B 18/203
                                                             606/9
(Continued)

FOREIGN PATENT DOCUMENTS

DE           19518807       12/1995
WO         WO 94/04116       3/1994
(Continued)

OTHER PUBLICATIONS

International Preliminary Report on Patentability Dated Oct. 15, 2020 From the International Bureau of WIPO Re. Application No. PCT/IL2019/050114. (9 Pages).
(Continued)

*Primary Examiner* — Jaymi E Della

(57) ABSTRACT

Described herein is a handheld skin treatment device (10) that delivers electromagnetic and/or electrical energy and fluid to a person's skin via a surface region (34) on the device; and a replaceable cartridge (40). The cartridge has a spout (42) having a tip (44). The device (10) has a locating feature (70) to position a tip at an opening (39) within the surface region. The spout may have a bend (53) and/or may meet a barrel of the cartridge at a location (51) that is laterally offset with respect to central longitudinal axis (47) of the barrel.

15 Claims, 12 Drawing Sheets

(52) U.S. Cl.
CPC ............... *A61B 2018/00696* (2013.01); *A61B 2018/00773* (2013.01); *A61B 2018/0091* (2013.01); *A61B 2018/1467* (2013.01); *A61B 2218/002* (2013.01)

(56) References Cited

U.S. PATENT DOCUMENTS

| | | |
|---|---|---|
| 2010/0063565 A1 | 3/2010 | Beerwerth et al. |
| 2011/0125146 A1* | 5/2011 | Greeley ................. A61B 18/14 606/33 |
| 2011/0144410 A1 | 6/2011 | Kennedy |
| 2013/0158547 A1* | 6/2013 | David .................... A61B 17/54 606/41 |
| 2017/0100542 A1* | 4/2017 | Norton ............... A61M 5/31511 |

FOREIGN PATENT DOCUMENTS

| | | |
|---|---|---|
| WO | WO 2005/110266 | 11/2005 |
| WO | WO 2009/104178 | 8/2009 |
| WO | WO 2019/193586 | 10/2019 |

OTHER PUBLICATIONS

International Search Report and the Written Opinion Dated May 9, 2019 From the International Searching Authority Re. Application No. PCT/IL2019/050114. (16 Pages).

* cited by examiner

DEVICE AND CARTRIDGE FOR SKIN TREATMENT

RELATED APPLICATIONS

This application is a National Phase of PCT Patent Application No. PCT/IL2019/050114 having International filing date of Jan. 29, 2019, which claims the benefit of priority under 35 USC § 119(e) of U.S. Provisional Patent Application No. 62/652,358 filed on Apr. 4, 2018 and U.S. Provisional Patent Application No. 62/755,489 filed on Nov. 4, 2018. The contents of the above applications are all incorporated by reference as if fully set forth herein in their entirety.

FIELD AND BACKGROUND OF THE INVENTION

The present invention relates to handheld devices and cartridges for skin treatment in which electrical and/or electromagnetic treatment technology and fluid is delivered to a person's skin. In some embodiments, the present also relates to a kit having a device and cartridge for such skin treatment.

A wide variety of cosmetic treatments are available to address various concerns people may have about their skin. These treatments include, amongst others, radio-frequency (RF) treatment, electroporation treatment (ELP), and low-level laser therapy (LLLT) treatment. RF and electroporation treatment involve application of electrical and/or electromagnetic energy to a person's skin using non-invasive electrodes that interface with the skin.

Electromagnetic energy may be supplied by one or more poles provided by a respective one or more electrodes. To concentrate the distribution of electromagnetic energy close to the surface the skin, rather than extending to underlying tissue, multiple electrodes may be employed, organized into one or more multi-pole groups. The poles may additionally or alternatively be used to supply electrical energy.

In the case of RF treatment, RF energy is supplied with a fluid between the electrodes and the skin to prevent burning of the skin. The fluid may also have properties that may be advantageous for skin health. For example, the fluid may be a gel comprising glycerin.

In electroporation treatment, a series of short electric pulses are delivered to the person's skin. The pulses apply an electric field across the skin cells to increase their permeability to a treatment fluid that is simultaneously applied to the skin. The fluid used in the case of electroporation treatment is different to that used for RF treatment. For example, in some applications, the treatment fluid used with electroporation is a serum comprising hyaluronic acid.

An object of the present invention is to solve one or more of problems of the prior art and/or to provide a useful market alternative.

SUMMARY OF THE INVENTION

A first aspect of the present invention provides a handheld skin treatment device that delivers electromagnetic and/or electrical energy and fluid to a person's skin via a surface region on the device, the device comprising:
  a device body comprising:
  a head comprising the surface region; and
  a cartridge containment portion comprising a container holding portion, and a path through the head, the path having a distal end, the distal end having an opening within the surface region;
  wherein the cartridge containment portion has a locating feature; and
  a replaceable fluid cartridge secured in the cartridge containment portion and having a rigid cartridge body that includes a spout extending through the path, wherein the locating feature positions a tip of the spout at the opening.

In some embodiments, the electromagnetic and/or electrical energy is more specifically electrical energy.

A second aspect of the present invention provides a kit for treating a person's skin, the kit comprising:
  a handheld skin treatment device for delivering electromagnetic and/or electrical energy and fluid to a person's skin via a surface region on the device, the device comprising:
    a device body comprising:
      a head comprising the surface region; and
      a cartridge containment portion comprising a container holding portion, and a path through the head, the path having a distal end, the distal end having an opening within the surface region; and
  a replaceable fluid cartridge for securing in the cartridge containment portion,
  wherein the cartridge containment portion has a locating feature and the cartridge has a rigid cartridge body that includes a spout, wherein when the cartridge is fitted in the device the spout extends through the path and the locating feature positions a tip of the spout at the opening.

The device according to the first aspect of the invention, or the kit according to the second aspect of the present invention, may have any one or more of the following features in any plausible combination.

In some embodiments, the cartridge containment portion comprises a cavity in the body and the container holding portion is within an enclosure in the body, wherein the path has a proximal end that is in fluidic communication with the container holding portion. By manipulating the device to have the enclosure in a closed configuration, the cartridge may be fully isolated from an environment external to the body of the device. In some embodiments the cartridge containing portion has an opening to the path that is large enough to allow the cartridge to be inserted into a secured position without having to twist the cartridge.

In some embodiments, the locating feature positions the tip beneath the surface region. Thus, it is ensured that the tip does not protrude from the head. For example, the tip may be set back from a most distal part of the surface region at the opening. At least part of the tip is, in any case, preferably visible from outside the opening to an unaided eye, for example from viewing at a distance of 30 centimeters beyond the opening.

Advantageously, having the spout extend to the opening mitigates against leaving fluid in the distal end of the path after removing the cartridge. This may improve hygiene and/or mitigate against blockage of the path. Furthermore, in an event of a replacement cartridge containing a different fluid, the device may eject the different fluid immediately or nearly immediately, as there is little or no residual fluid in the path from the previous cartridge. Further, by having the tip at the opening but not extending beyond the opening, the surface region interfacing with the person's skin may be smooth, as there is no spout protruding from the surface.

Having a rigid cartridge body that includes a spout, and which therefore has a rigid spout, may facilitate a process of fitting a replacement cartridge. For example, the rigidity may aid the fitting process by facilitating a person's control over the location of the spout's tip when they hold the cartridge by the body. Further, the rigidity of the spout may provide resistance to frictional or other forces which may act on the spout when attempting to guide the tip of the spout to the opening.

Further, in each of the embodiments described herein, the path be or comprise a channel having a fixed shape for guiding the spout. The channel is in some embodiments elongate. The channel may extend an entire way through the head. Having an elongate channel may assist in replacing the cartridge by guiding the spout to the opening during when placing cartridge. However, a flexible spout may be difficult to thread through the channel, with frictional forces potentially preventing the tip of the spout from reaching its desired location at the opening. With a rigid spout, on the other hand, the spout's shape will not deform as it is pushed through the channel. Rather, the dimensions of the spout are controlled and consistent each time a replacement cartridge has been inserted into the device. One or more walls of the path may, in some embodiments, include one or more recesses or cavities along its length, but preferably the path, in any case, includes or consists of one or more walls (e.g. a wall having a curved profile, or plurality of distinct walls) that forms or that collectively form a channel for guiding the spout. Therefore, even in embodiments in which the path has a cavity, a channel may guide the spout so that it does not get caught in the one or more cavities/recesses. In other embodiments, however, the channel may form a continuous lumen along the whole length of the path. Such a lumen may have a cross sectional area that tapers toward the distal end of the path. In some embodiments, the locating feature comprises a stop in a distal end of the path, wherein the spout has a distal end abutting the stop to position the tip of the spout at the opening.

Having the locating feature in a distal end of the path may, in comparison with a more proximal location, advantageously better control the distance between the tip of the spout and the surface region of the head, due to dimensional tolerances, and to ensure that a seal is created at the opening. In some embodiments, the stop is provided by an inward tapering of the path at a distal end of the path.

In some embodiments the stop seals against distal end of the spout. By way of the seal, leakage of the fluid back into the path may be mitigated.

In some embodiments, the path is formed by a plurality of parts, the plurality of parts including a resilient member that forms the stop. The use of a resilient member may be advantageous in providing the seal against the distal end of the spout. However, in other embodiments, the stop is rigid.

In some embodiments, the stop abuts the distal end of the spout by abutting the tip of the spout.

In other embodiments, the locating feature comprises a wall of container holding portion that limits movement of the cartridge body towards the opening by acting as a stop against part of a container portion of the cartridge.

In some embodiments the channel has a cross sectional area that increases toward the container holding portion. The increasing cross-sectional area may facilitate movability of the cartridge body when the spout is in the channel to accommodate the cartridge body in a plurality of orientations when the tip of the spout is at, or at least proximal to, the opening. For example, the path may be funnel shaped, and in some embodiments, the funnel shape may include a bend. Further the bent tunnel, in some embodiments, is shaped to include a line of sight through the path. The line of sight can may advantageously be used to visually verify whether the path is blocked, especially in the case of the path being elongate. The line of sight may be included despite the bend, and may facilitate insertion of the cartridge into a preliminary insertion position with the tip of the cartridge at the opening, and to then twist the cartridge, for example by 90 degrees or about 90 degrees, to a secured position in the body with the tip at the opening.

In some embodiments, the rigid body further comprises a container that forms a bulk of a cartridge volume. In some embodiments the container is a barrel.

In some embodiments, the spout is elongate. Having an elongate spout is in advantageous in some embodiments by enabling the container to be set back from the surface region of the head. This may facilitate the inclusion of a plurality of sensors and/or a plurality of different energy delivering means in the head, as such inclusions which may require a thicker head. In some embodiments of the present invention, the skin-treatment device is configurable to selectively deliver any of a plurality of types of energy without needing to change the head.

For example, in some embodiments, the head includes a plurality of electrodes wherein the device is configurable to selectively deliver an energy type from a group comprising (i) RF treatment energy and (ii) electroporation treatment energy.

In another example, the head may include one or more lasers for delivering LLLT treatment energy and may also include a plurality of electrodes for delivering any one of (i) RF treatment energy and (ii) electroporation treatment energy or selectively for delivering an energy type from a group comprising (i) RF treatment energy, (ii) electroporation treatment energy, and (iii) LLLT treatment energy.

In some embodiments, said opening in the surface region is an opening in a part having an appearance as one of said electrodes.

In some embodiments, the electrodes are spaced along a notional ring. In some embodiments the ring is a circle. In some embodiments, at least one light source is positioned to emit light from within the notional ring to heat the person's skin with the light.

In some embodiments, the spout has a bend. In some embodiments, the spout has a first straight portion on a distal side of the bend. The first straight portion is, in some embodiments, elongate. In some embodiments, the spout may additionally or alternatively have a second straight portion on a proximal side of the bend, being a side of the bend that is opposite the distal side and is proximal to the barrel. The second straight portion is, in some embodiments, elongate. In some embodiments in which the spout has the bend, the spout has only one bend.

In some embodiments, the path has a wall having a bend that turns in a common direction with the bend in the spout to assist in guiding the spout to the locating feature.

The locating feature can secure the cartridge in its desired location with little or no risk that that the cartridge will fall out of the position if they move and/or reorient the device.

In some embodiments, a wall of the body is displaceable to expose the container holding portion to allow the cartridge to be replaced, wherein at least during replacement the head is fixedly connected a portion of the body that includes the container holding portion. Thus, the cartridge may be replaced without having to remove the head from the rest of the body.

In some embodiments, the wall that is displaceable is a laterally facing portion of the enclosure.

The displaceable wall may be removed and/or moved to access a cartridge in the enclosure. The locating formation may in such embodiment be located on a wall of the enclosure that is not the displaceable wall.

In some embodiments, the device body further comprises:

at least one sensor for sensing an identification on the cartridge;

a motor for driving an actuator against the cartridge to eject fluid from the cartridge via the opening; and a processing system configured to:
  detect the identification using the at least sensor;
  drive delivery of the electromagnetic and/or electrical energy according to a selected one of a plurality of energy types; and
  based at least in part on the detected identification, and control the motor in manner tailored to said selection.

In some embodiments, the processing system is configured to limit the motor to execute a fluid ejection procedure only once for the replaceable cartridge. Thus, the device is configured to enforce or at least aid in enforcing single use of the cartridge, whereby the cartridge needs to be replaced before the processing system permits the motor to again execute the fluid ejection procedure.

The fluid ejection procedure may comprise one or more motor steps that exert pressure on cartridge.

To enforce single use, in some embodiments, upon removal of the cartridge, the processing system detects said removal, for example using the at least one sensor. The processing system only instructs the fluid ejection procedure once the processing system detects a replacement cartridge having a different identification to the removed cartridge.

Additionally or alternatively, to enforce single use, in some embodiments, the actuator automatically retracts upon completing execution of the fluid ejection procedure, wherein the processing system is configured to deem that the ejection procedure is completed upon detecting any one of the following events:
  a) that the actuator has been actuated to expel all fluid from the cartridge, e.g. by moving a predefined maximum number of required steps for full expulsion of the fluid; or
  b) that a predetermined maximum duration of time has elapsed since an earlier stage event in the fluid ejection procedure, for example, since starting of the ejection procedure or since stopping the ejection procedure.

In some embodiments, the processing system is configured to receive an operational parameter from a user, e.g. from a remotely controlled interface such as a smartphone or tablet, and control the motor to execute the fluid ejection procedure at a speed that is based on the received operational parameter.

Further, in some applications of the invention it is desirable for the fluid in cartridge to be evenly distributed between left and right sides of a person's face. In some embodiments, the device is configured to output an indication to the user, such as an audible sound, indicating to the user that the device should be moved from one side of the face to the other side of the face.

In some embodiments the at least one sensor is a radio frequency identification (RFID) reader.

In some embodiments, the spout has a lumen of a substantially constant cross-sectional area, e.g. a constant diameter.

In some embodiments, the container holding portion has a contoured wall shaped to complementarily match a barrel of the cartridge.

In some embodiments the head has a face with a normal axis that extends in a direction that is angled with respect to a longitudinal axis of the housing, wherein a line of sight of through the path extends through the head at an angle that is parallel, or at least generally parallel, to the normal axis. In some embodiments, the angling of the normal axis with respect to the longitudinal axis may match an angling of the first bend.

In some embodiments, the locating feature is at an opposite end of the cartridge containment portion to the opening within the surface region.

In some embodiments the spout is integrally formed with the container. For example, in some embodiments, the spout and barrel is formed from as a single injection molded part, i.e. formed in one mold. Compared with a separately molded barrel and spout, the use of a single mold may strengthen the spout.

In some embodiments, the cartridge comprises a locating feature at the second end of the elongate barrel and shaped to stabilize the cartridge body in a specific orientation within the device.

In some embodiments, the elongate barrel is a cylinder, and the locating feature and the elongate spout are spaced about the cylinder at an angle in a range between 135 and 225 degrees, and in some embodiments, more specifically 180 degrees, or about 180 degrees.

In some embodiments, the cartridge includes an electronically readable unique identification tag. In some embodiments the tag is a radio frequency identification (RFID) tag.

The elongate barrel and the elongate spout may both be comprised of, consist of, or consistent essentially of, a plastic or other polymer, for example in some embodiments, polypropylene.

In accordance with a third aspect of the present invention there is provided a fluid-filled cartridge for use in a handheld skin treatment device, the device having an actuator, in the form of a plunger, for ejecting fluid from the cartridge, the cartridge comprising:
  a rigid cartridge body comprising:
  an elongate barrel holding the fluid and extending along a first central longitudinal axis; and
  an elongate spout extending from a first end of the barrel; and
  a plunger cap sealing a second end of the elongate barrel and that is opposite the first end of the elongate barrel, the plunger cap being slidable within the elongate barrel to eject the fluid from the spout when pressed by the plunger cap,
  wherein the elongate spout meets the barrel at a location that is laterally offset with respect to the central longitudinal axis.

The lateral offsetting of the location may enable a more efficient use of space within a body of the device in which the cartridge is held in use. Further the lateral offsetting may facilitate an easier process of fitting of the cartridge into the body.

In some embodiments, an elongate spout extends from said location in a second longitudinal axis that is generally parallel to, and laterally offset from, the first longitudinal axis.

In some embodiments, the distal end of the elongate spout extends along a third longitudinal axis that is angled with respect to the second longitudinal axis.

In accordance with a fourth aspect of the present invention there is provided a fluid-filled cartridge for use in a handheld skin treatment device, the device having an actuator, in the form of a plunger, for ejecting fluid from the cartridge, the cartridge comprising:
  a rigid cartridge body comprising:
  an elongate barrel holding the fluid and extending along a first longitudinal axis; and
  an elongate spout extending from a first end of the barrel; and a plunger cap sealing a second end of the elongate barrel and that is opposite the first end of the elongate barrel, the plunger cap being slidable within the elongate barrel to eject the fluid from the spout when pressed by the plunger cap,
wherein the spout has a bend.

In some embodiments, the spout has a first straight portion on a distal side of the bend. The first straight portion is, in some embodiments, elongate. In some embodiments, the spout may additionally or alternatively have a second straight portion on a proximal side of the bend, being a side of the bend that is opposite the distal side and is proximal to the barrel. The second straight portion is, in some embodiments, elongate. In some embodiments in which the spout has the bend, the spout has only one bend.

Preferably, the elongate spout meets the barrel at a location that is laterally offset with respect to the central longitudinal axis.

The cartridge of the third or fourth aspects of the present invention may have any one or more of the features of the cartridge of the first or second aspect of the present invention, and the features may be in any plausible combination.

In any case, the cartridge spout is preferably integrally formed with the barrel.

In some embodiments, a gripping member extends from the second end of the elongate barrel for pulling the cartridge from the device. In some embodiments the gripping member is a flexible tag. The flexible tag may, for example be formed from at least one end of an elongate sheet of material, for example a paper or plastic, that wraps around a proximal end of the cartridge.

The cartridge in the device of the first aspect of the invention or in the kit of the second aspect of the present invention may have any one or more of the features of the cartridge of the third or fourth aspect of the present invention, and such features may be in any plausible combination.

Further it will be appreciated that other aspects of the invention include any non-transient computer readable memory, whether distributed or not, wherein the memory has a program store for storing code which is readable by a processing system to configure the processing system to operate as a processing system in accordance with any embodiment of the invention disclosed herein.

Further it will be appreciated that further aspects of the invention includes methods for operating a device in accordance with any embodiment of the invention disclosed herein.

As used herein, except where the context requires otherwise, the terms "comprises", "includes", "has", and grammatical variants of these terms, are not intended to be exhaustive. They are intended to allow for the possibility of further additives, components, integers or steps.

Various embodiments of the invention are set out in the claims at the end of this specification. Further aspects of the present invention and further embodiments of the aspects described in the preceding paragraphs will become apparent from the following figures and description, given by way of non-limiting example only. As will be appreciated, other embodiments are also possible and are within the scope of the claims. Like reference numerals in different drawings are used to indicate either the same or alike parts.

DETAILED DESCRIPTION OF THE EMBODIMENTS

Figure 1:
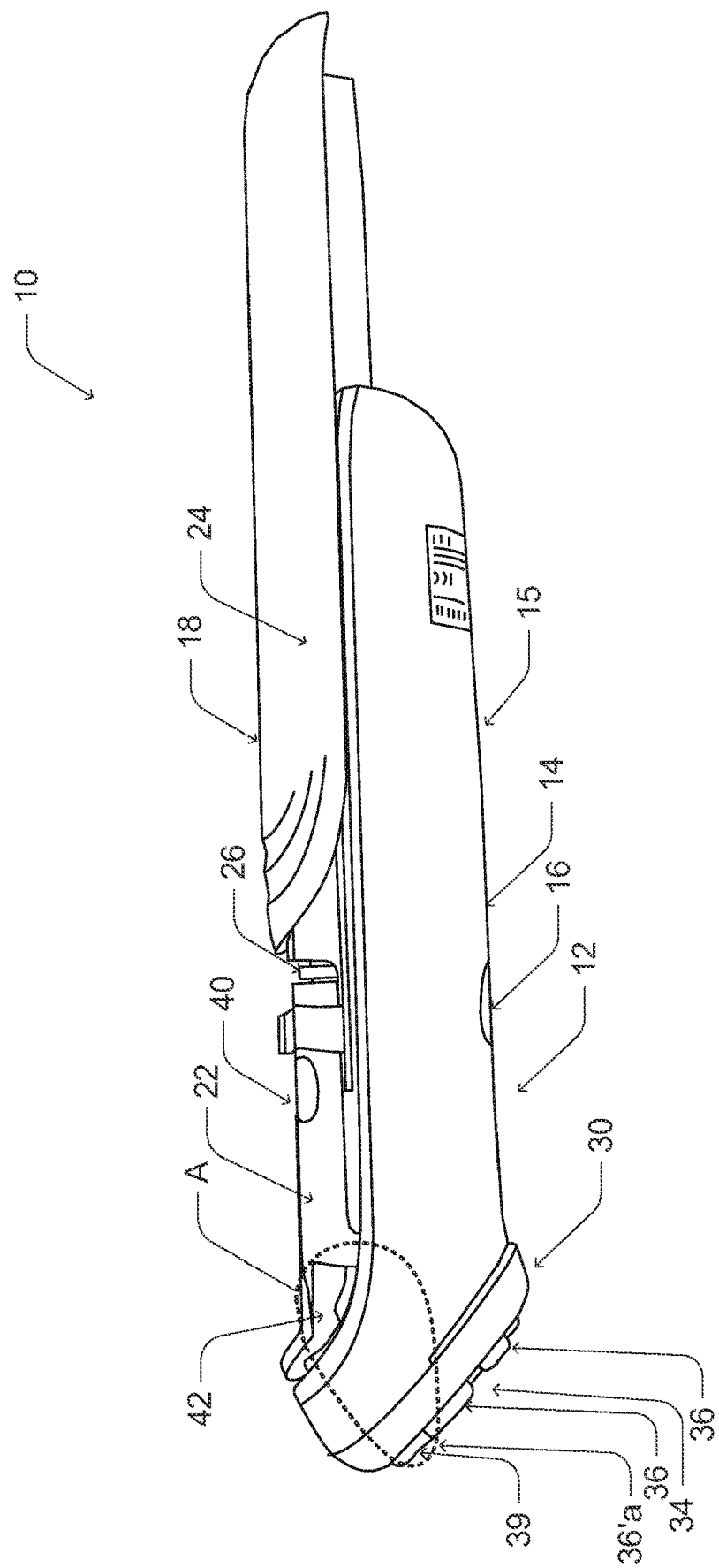
FIG. 1 is a side view of a skin treatment device having a displaced cover showing to show a replaceable cartridge secured in the device in accordance with one or more aspects of the present invention.

An exemplary embodiment of a skin-treatment device 10 in accordance one or more aspects of the present invention is illustrated in FIG. 1. The device 10 has a body 12 that is shaped and sized to be handheld. The body has a main portion 14 that is cylindrically shaped for easy holding by a person. The main portion 14 includes control electronics (FIG. 7) and a motor for pressing fluid from a replaceable cartridge 40 in the device 10. A bottom wall 15 of the main portion 14 has an actuation button 16 and for user actuation of the device. The main portion also has a displaceable top wall 18 that is slidable to an opened position, as shown in FIG. 1, with respect to the bottom wall 15 to open an enclosure 22 in which is held the replaceable cartridge 40. From the opened position the displaceable wall 18 slides longitudinally to close the enclosure and thereby fully contain the cartridge 40 within the body 12. In other embodiments the cover of the enclosure is displaceable by being fully separable from the rest of the body 12. From a rear end 24 of the main portion 14 of the body the motor drives a plunger actuator having a disk 26 at a front end of a shaft (not shown) for pushing against the cartridge 40 to expel fluid from the cartridge 40 onto a person's skin.

The body 12 also has a disc shaped head 30 at its front end. The rear end of the head receives a cartridge spout/nozzle 42 that extends to an opening 39 in a surface region 34 for interfacing with the person's skin by contacting the skin, either directly or via fluid ejected from the cartridge 40. The surface region 34 is a face of the head 30 from which plurality of sources provide of electromagnetic and/or electrical energy of different types. The head also includes an electronic board 32 (FIG. 4) for interfacing with the sources. The sources include a plurality of electrodes 36 and a plurality of light sources 38 in the form of lasers (FIG. 5).

The electrodes 36 are configured as a plurality of bi-polar electrodes pairs that rise from an annular surface 31, whereby the electrodes 36 are spaced along a notional circular ring with adjacent electrodes being of opposite poles. Since the electrodes 36 rise from the annular surface 31, the surface region 34 that interfaces with the person's skin has undulations—the annular ring may interface the person's skin, in addition to the electrodes. However, on average, the surface region 34 has a normal axis 11 that is perpendicular to skin-facing surface 13 of the annular ring. The electrodes 36 in the surface region 34 can selectively provide electric pulses for electroporation therapy or RF fields for RF therapy.

The light sources 38 are positioned to emit light from a region 33 that is recessed from the surface region 34. The recessed region 33 is recessed beneath a window (not shown) in the annulus of the annular ring. Such an arrangement may reduce an amount of stray light from the device during application of LLLT. The light includes a plurality of narrowband frequencies from different sources. For example, the light in some embodiments has spectrums focused on 430 nm light to treat acne, 530 nm light for skin pigmentation treatment, or a combination of 650 nm and 850 nm for anti-aging treatment. Thus, as shown in the example of FIG. 5, there are four light sources.

With the cartridge 40 held in the enclosure, a distal tip 44 of the cartridge spout 42 is positioned at the opening 39 in the surface region 34. The tip 44 is positioned to be slightly beneath the surface 34 so that the tip 34 does not protrude and provide discomfort or a scratch risk to the person's skin. Thus, although the tip is at the opening there may be a small distance to the surface region 34, e.g. than less 3 mm, less than 2 mm, or less than 1 mm, in some embodiments, and/or by a distance that is less than a width (e.g. diameter) of the opening, in some embodiments.

In the exemplary embodiment of FIG. 5 the opening in the surface region 34 is provided by an aperture in a part/component 36'a, which is a cartridge port having an appearance (i.e. from outside the device) as one of the electrodes 36. It appears as one of the electrodes by having a similar or matching shape (as viewed from outside the device) to at least one of the electrodes 36 and having a metallic external surface, which may be provided by a metallic coating. Such a coating may consist of, for example, 30 micron Copper, 6 micron nickel and 0.6 micron chrome.

The part 36'a is in some embodiments an electrically isolated component, as distinct from the electrodes. Having the tip at the opening has an advantage of minimizing residual fluid within the head 30, which may reduce the risk of blockage of the opening 39 and/or may improve hygiene. Further a cartridge with one kind of fluid may be used with one type of treatment/therapy, such as electroporation therapy, and a cartridge with another kind of fluid may be used with another type of treatment/therapy, such as RF therapy. By having the tip of the cartridge extend to the surface 34, dead space in the cartridge body is small, so there may be little or no residual fluid from an old cartridge present when a replacement cartridge is inserted.

Figure 2:
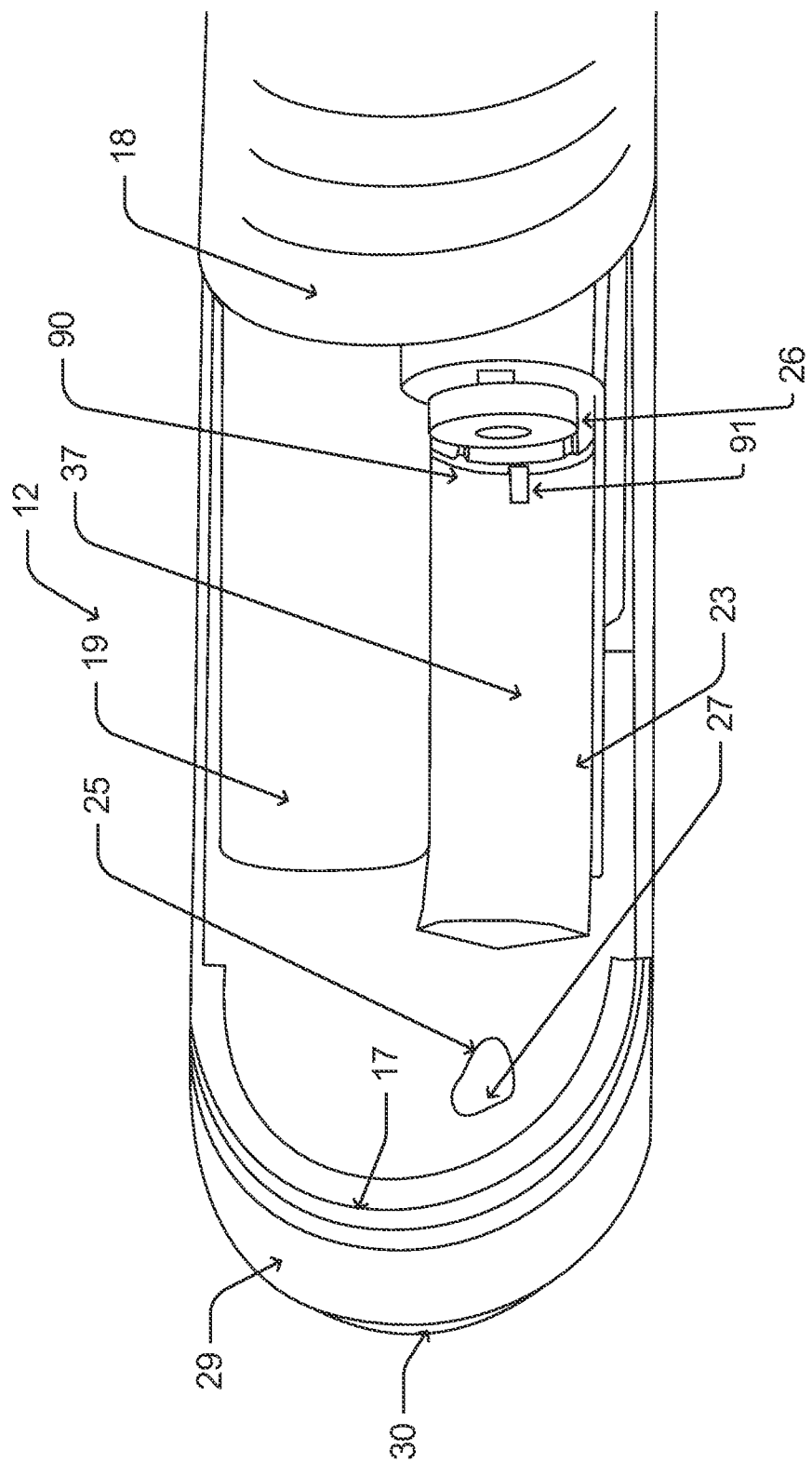
FIG. 2 is a top view of a front part of the skin treatment device of FIG. 1 but with the cartridge absent from the device.

A front portion of the device's body 12, with the cartridge 49 absent from the enclosure 22, is shown in FIG. 2. The enclosure 22 is shown in an open configuration, exposing a container holding portion 23 and an opening 25 to a path 27 that extends through front end 29 of the body, including through the head 30. The container holding portion 23 has a base 37 that is contoured to complement the side of the container it is designed to hold, the container being a barrel in the exemplified embodiment. The container holding portion 23 has a locating feature 91 in the form of an opening at a rear end 90 of its base 37, which is adjacent the disk 26 at the end of the plunger actuator. A rechargeable battery for powering the device's electronic and mechanical components is housed parallel the container holding portion, beneath a raised portion 19 of a plastic molding that forms the base 37. The container holding portion is enclosed by the body 12 by sliding the top wall 18 from its open position shown in FIG. 2 to engage with a ridge 17 in the front end 29 of the body 12.

An embodiment of a replaceable cartridge, exemplified by cartridge 40, which may be fitted to the device 10 is illustrated in FIG. 2, in a side sectional view. The cartridge 40 has a rigid plastic body 43 that includes a container portion 46, in the form of barrel having a central longitudinal axis 47, and includes the spout 42 which extends from a front side 48 of the container 46. At is base, the spout 42 extends along an axis 49, which is parallel to the central longitudinal axis 47. However, the spout extends from a location 51 that is laterally offset from the central longitudinal axis 47. The spout has a bend 53 that directs the distal end 55 of the spout to extend to its distal tip 44 along a further axis 57 that is at an angle that is between of 40 and 50 degrees from the axis of extension 49 at the spout's base. For strength, the body 43 is a single part, being formed in a single molding.

When the cartridge is new, the barrel 46 has a disk-shaped and resilient silicon plunger cap 58 fitted within a rear end 59 of the barrel 46. The plunger cap has two annular lips 60 for sealing against the inner wall of the barrel to hold a pre-filled fluid 21 within the barrel 46. The barrel has a rear opening 62 that receives the plunger gap during manufacture of the cartridge. In use, the disk 26 at the front end of the plunger actuator pushes against the plunger cap 58 to expel fluid 21 from the tip 44.

The rear end 59 of the cartridge body 43 has a laterally protruding locating formation 64 shaped for a mating engagement with the locating feature 91 in the base 37 of the container holding portion 23 of the device 10.

Figure 3A:
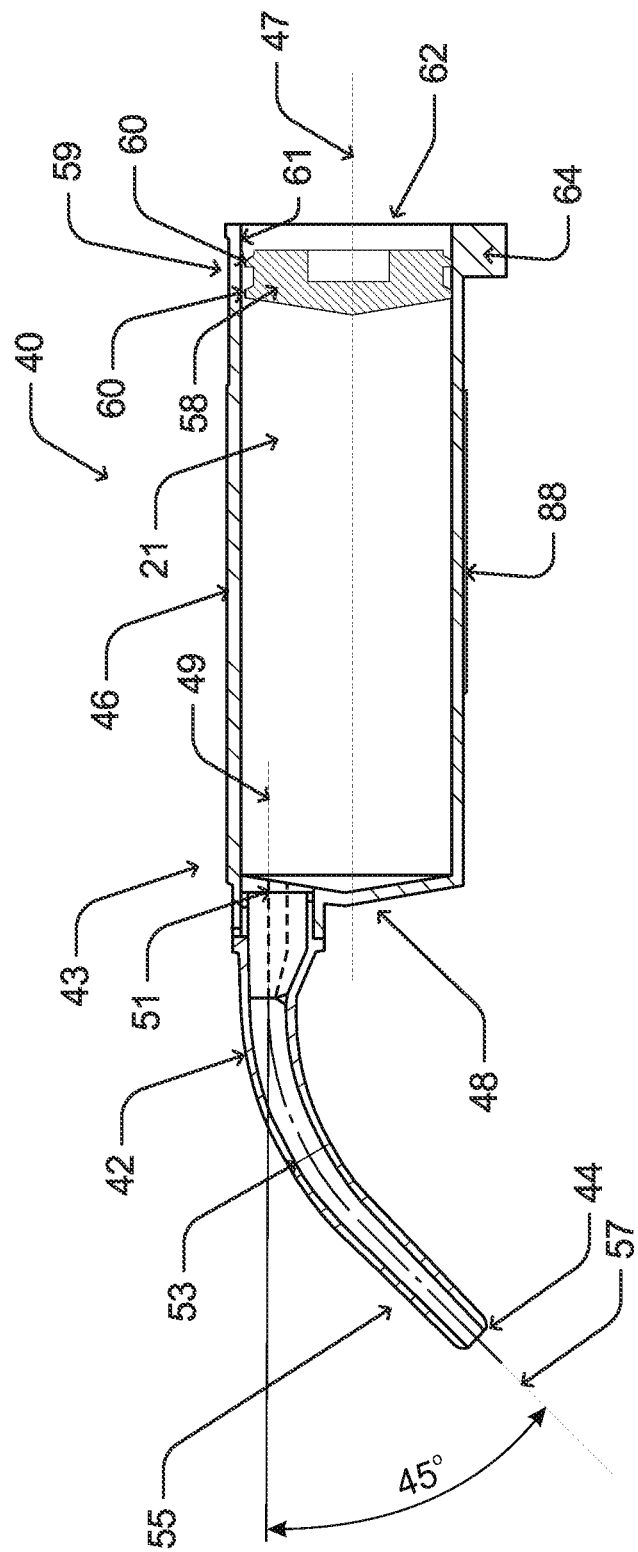
FIG. 3A is a side sectional view of the cartridge illustrated in FIG. 1.
Figure 3B:
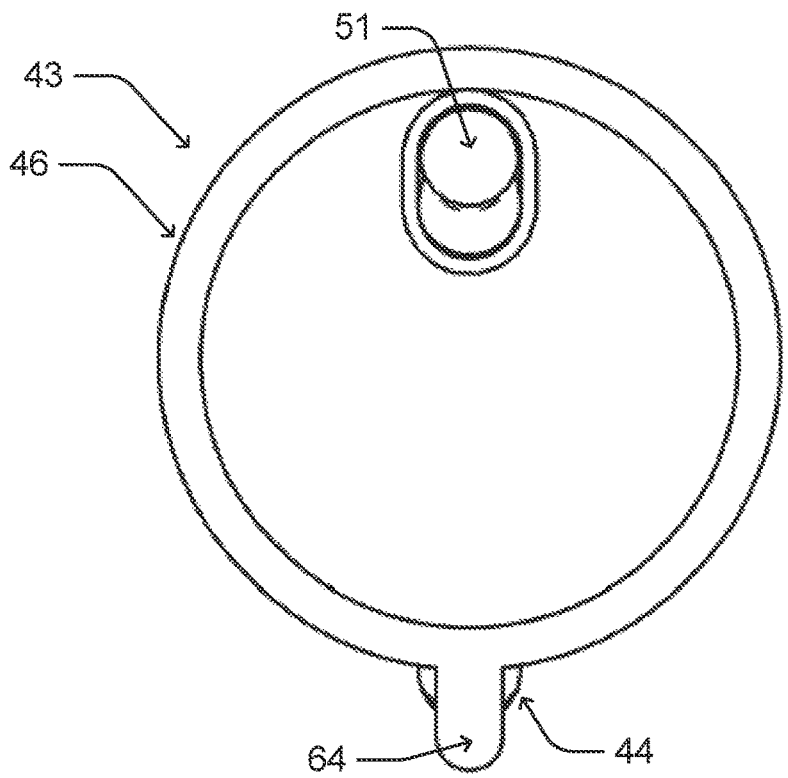
FIG. 3B is a rear view of the cartridge illustrated in FIG. 1.
Figure 3C:
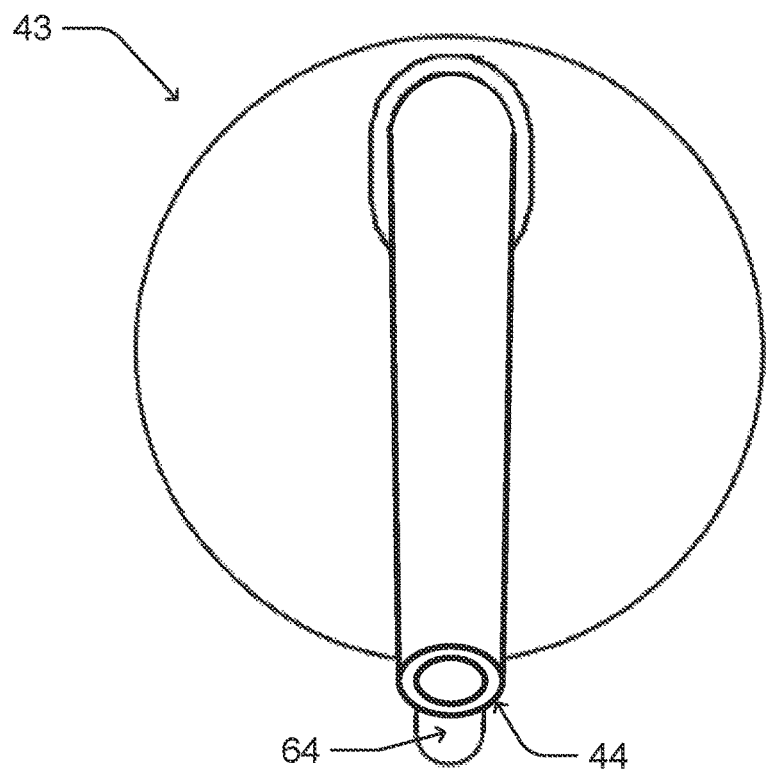
FIG. 3C is a front view of the cartridge illustrated in FIG. 1.

FIG. 3B shows a rear view of the cartridge body 43 with the plunger cap 58 absent. As can be seen in this view, the locating formation 64 is displaced by 180 degrees with respect to the location 51 from which the spout extends from the barrel. Thus, when the cartridge 40 is positioned in the body 12, the location 51 is adjacent the displaceable side wall 18 when the wall 18 covers the cartridge 40. However, due to the bend in the spout, the tip 44 of the spout 42 is at the same angular position about the barrel 26 as the locating formation 64, as best illustrated by FIG. 3C, which shows a front view of the cartridge 40.

Figure 4:
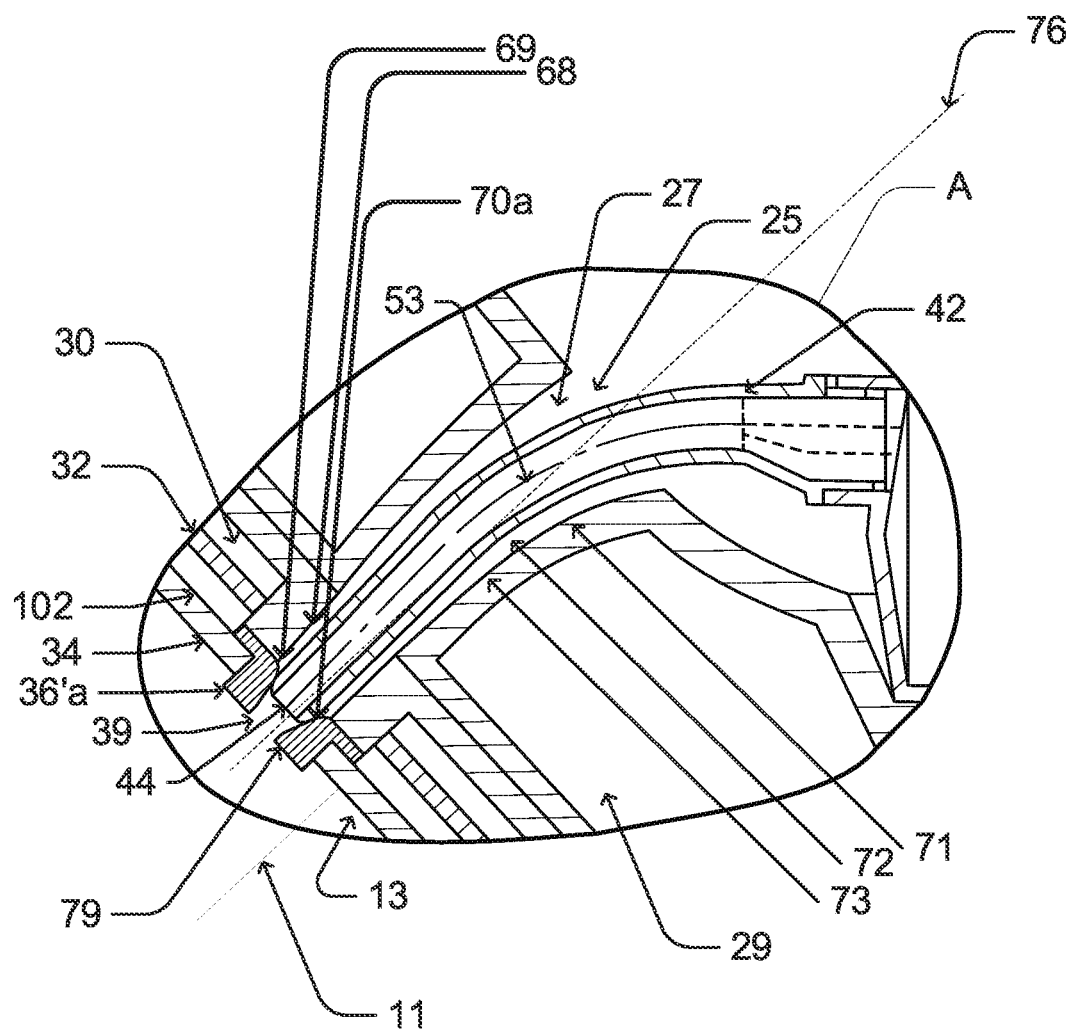
FIG. 4 is a part of a side sectional view of a front end of a skin treatment device in accordance with FIG. 1 that contains the replaceable cartridge.
Figure 5:
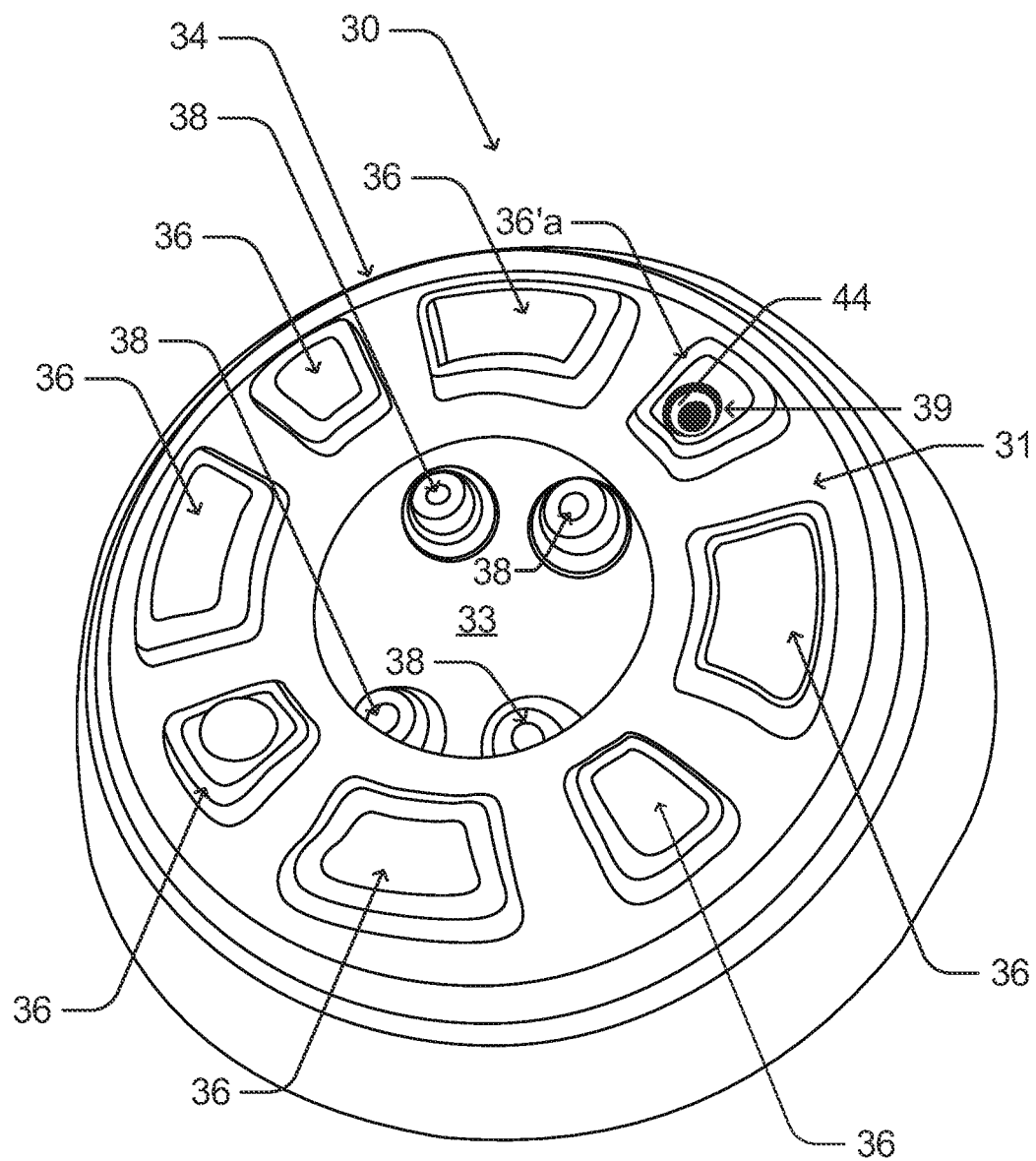
FIG. 5 is front view of the device of FIG. 1 showing a head of the device, the head having a front face for interfacing with a person's skin.

FIG. 4 shows a sectional view of a portion of the front end 29 of the device's body with the cartridge secured in the body. The figure shows the path 27 as a channel with a continuous lumen and shows the spout 42 extending through it such that the tip 44 of the spout 42 is at the opening 39 in a component 36'a that forms part of the skin-interfacing surface region 34 of the head 30. However, the tip 44 is set back slightly from a distal section 79 of the surface region 34 that is adjacent the tip 44 and is also at the opening. For illustrative ease of illustration, the electrode 36'a is shown in FIG. 4 as having sharp corners in the surface 34, but it will be appreciated that in various embodiments, the corners are more preferably chamfered.

The channel 27 tapers inwardly, essentially continuously along its length, from the opening 25 at the cartridge enclosure to the opening 39 in the surface region 34. The tapering is most pronounced towards the respective channel openings 25 and 39. At the distal end 68 of the channel, the tapering acts as a stop 70a for the tip 44. The tapering of the stop is such that the diameter of the channel 27 is wider than the outer diameter of the tip 44 at an inward end 69 of the stop, and is less than the outer diameter of the tip 44 at the opening 39. In some embodiments the tapering of the stop is at an angle of more than 10 degrees and less than 30 degrees, for example 20 degrees. In other embodiments the angle is between 5 and 10 degrees. In the illustrated embodiment, the stop is provided by a surface of a component that forms the relevant part 36'a, looking like an electrode 36. However, in other embodiments, the stop may be formed by a component forming part of the channel but that does not have the appearance of an electrode. To seal or assist in sealing the channel 27 against rearward ingress of fluid expelled from the tip 44, the stop 70a is in some embodiments provided by a resilient material, for example, silicon. However, in other embodiments, the stop 70a is made of a rigid material that seals against the plastic tip 44.

Figure 8:
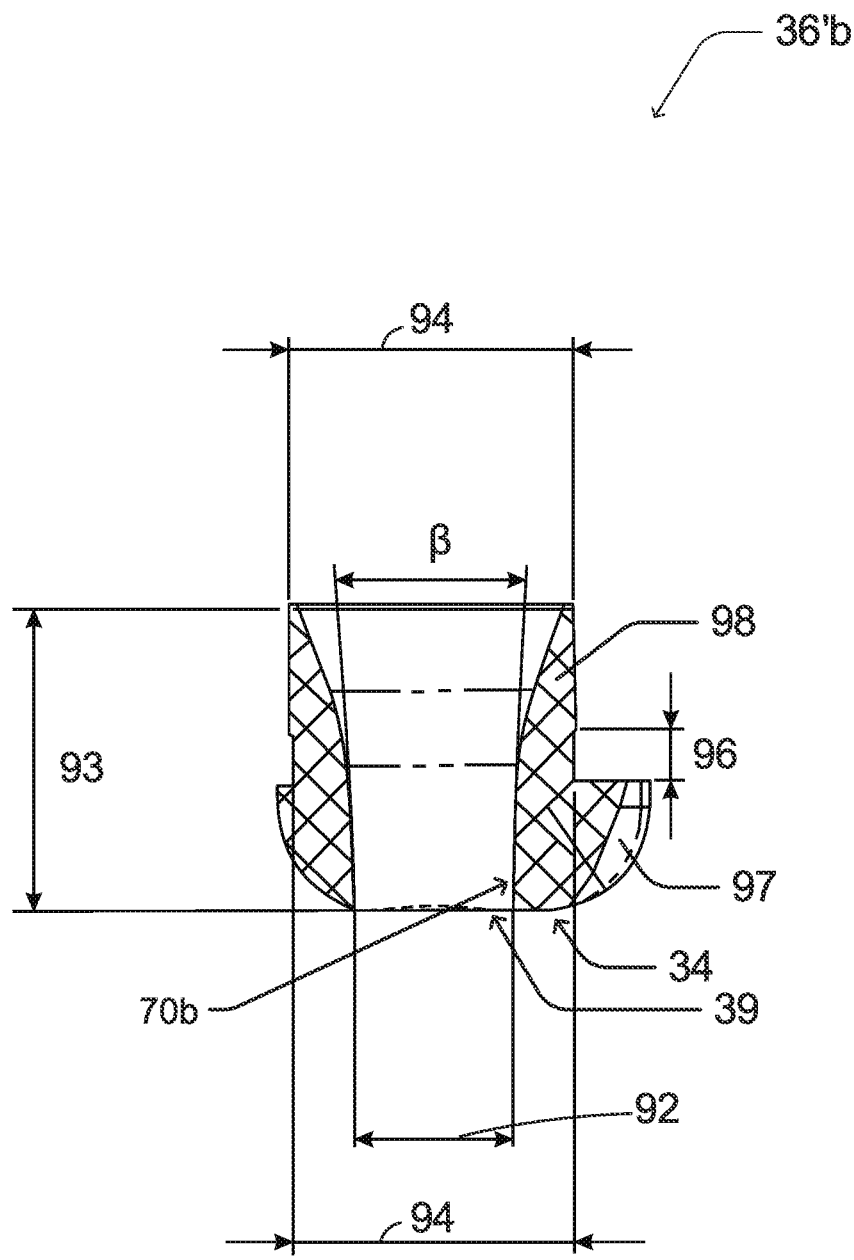
FIG. 8 is a side cross sectional view of an exemplary cartridge port in accordance with one more embodiments of the invention.
Figure 9:
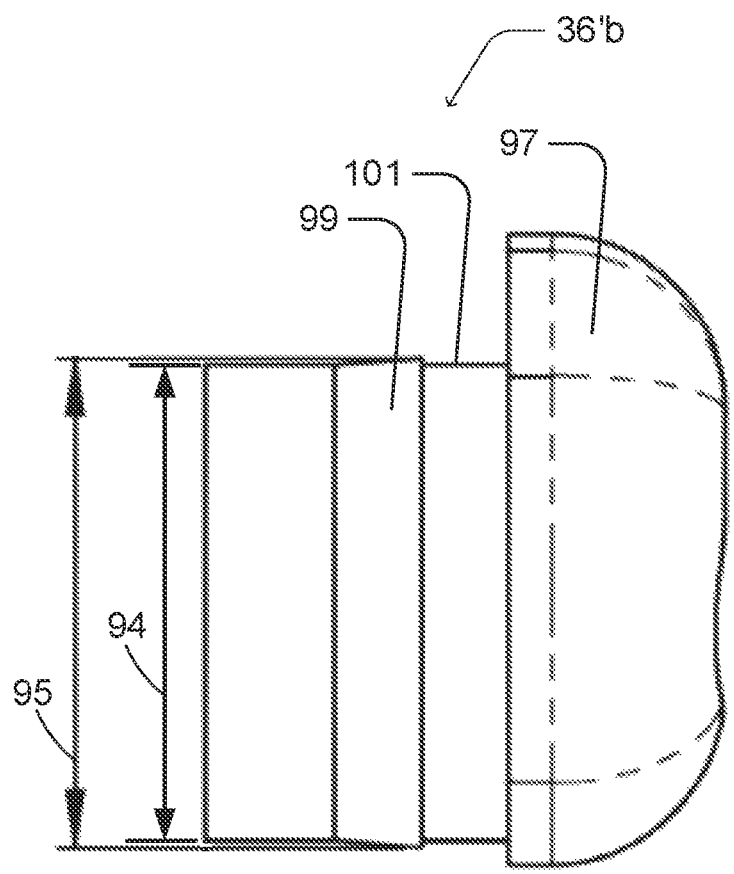
FIG. 9 is an external side view of the cartridge port of FIG. 8.

FIG. 8 shows a side cross sectional view of another part 36'b having the appearance of an electrode 35 and which may be used instead of part 36'a. In this example part 36'b is a molded part made of a rigid plastic which, like part 36'a forms a seal against the tip 44 of the spout 42, and may have the same metallic coating as already described herein.

In one or more exemplary embodiments, the molded part 36'b has an internal diameter 92 at the opening 39 of the surface region 34. The part 36'b has a depth 93 that is greater than the diameter, in the illustrated example. The stop 70b in the part 36'b is provided by a lumen having a draft angle 94 of 0 (e.g. an angle between 5 and 10 degrees) extending inwardly from the opening 39. The tip 44 of the spout 42 has an outer diameter of slightly wider than the inner diameter 92 such that insertion of the tip 44 towards the opening 39 is stopped by the stop 70b with the tip 44 being about 1 mm shy of the surface 34 at the opening 39.

The part 36'b has a head/boss 97 protruding from a neck portion 98 having an outer shape of a cylinder of a diameter 94 along its length (the diameter 94 being greater than the diameter 92) except for a wedge region 99. The wedge region 99 is in or close to the center of the cylinder and extends outwardly towards the boss 97 whereby a recess 101 is formed between the wedge region 99 and the head 97. During assembly, the neck portion 98 is inserted into a hole in a mounting panel 102' in the head 30' of another embodiment of a front end 29' of the device 10. The front end 29' is essentially the same as front end 29, albert shown in more detail, but a path 27' having a slightly different shape to path 27 of FIG. 4. During assembly, the wedge portion 98 of part 36'b resiliently deforms while the neck portion 98 is pushed through the hole in the mounting panel 102', and then returns to its pre-deformed dimensions to hold the part 36'b in place, mounted to the mounting panel 102'. As will be appreciated to the person skilled in the art, the part 36 may in other embodiments be mounted to mounting panel or to another part by an alternative mechanism, e.g. glue, one or more screw etc.

Figure 10:
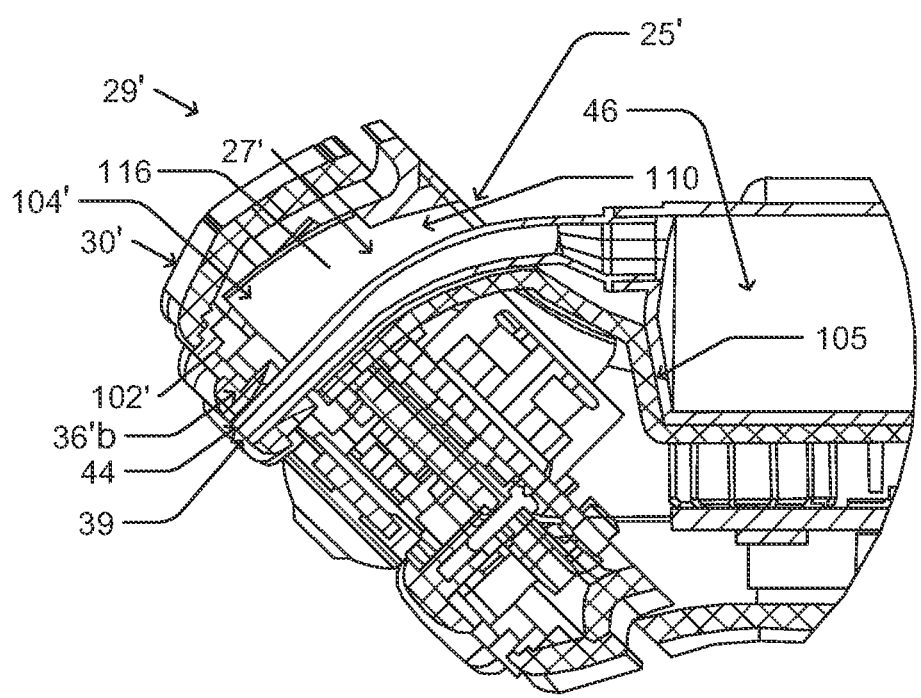
FIG. 10 is a side sectional view of another embodiment of a front end of a skin treatment device in accordance with FIG. 1 which includes the cartridge port of FIG. 8.
Figure 11:
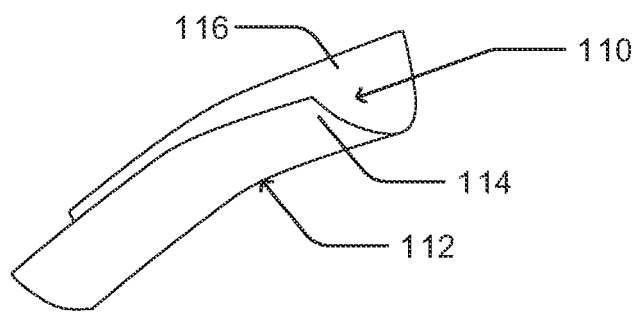
FIG. 11 is a perspective view of an exemplary channel in a path through a head of the front end shown in FIG. 10.

In the example of front end 29' of FIG. 10 the path 27' includes a cavity/recess 104', in contrast with the channel 27 of FIG. 4 which is a smooth lumen. The path 27' includes a channel 110 formed by a curved wall 112 (FIG. 11) having a U-shaped cross section. The wall 112 includes generally opposed side-portions 116 (also shown in FIG. 10) and 114. In other embodiments the cross section may be V shaped, and the two arms of the V may be generally opposed in the sense of the vertex of the V being less than 90 degrees. The wall(s) 112 of the channel are shaped to guide the tip 44 of the spout to the opening 39, either directly or, as in embodiment shown in FIG. 10, via part 36'. By sliding the tip along the wall(s) 12 of the channel, a person inserting the cartridge (e.g. using the method described below) can easily avoid getting the tip 44 getting caught of the cavity 104'. The path 27 or 27' through the front end 29 or 29' of the device is shaped to provide a line of sight 76 through the channel 27, 27'. In some embodiments, the line of sight enables at least a majority, and in some embodiments all, of the opening 39 at the surface region 34 to be seen though the opening 25 to the cartridge enclosure when the cartridge 40 is absent from the device 10. In the case of channel 27, a wall portion 72 is similarly shaped to wall 27' in that both versions provide a channel and include a bend along their length. However, despite the bend a line of sight is provided to the opening 39 enables visual inspection of the channel.

When inserting a replacement/new cartridge 40, the cartridge may be first inserted to a preliminary position (e.g. as shown in FIG. 1) in which the cartridge is not yet held in the container holding portion 23 of the body 12, yet the tip 44 is against the stop 70a. The cartridge container/barrel 46 is then moved into the container holding portion 23 where it is secured by virtue of a mating between the locating formation 64 on the cartridge and the locating feature 91 in the container holding portion 23. Starting from the position shown in FIG. 6A the cartridge is twisted by about 90 degrees to move it into its secured position. However, the opening 25 or 25' is large enough to allow the cartridge to be alternatively be inserted into the secured position of FIG. 6A without having to twist the cartridge.

Figure 6A:
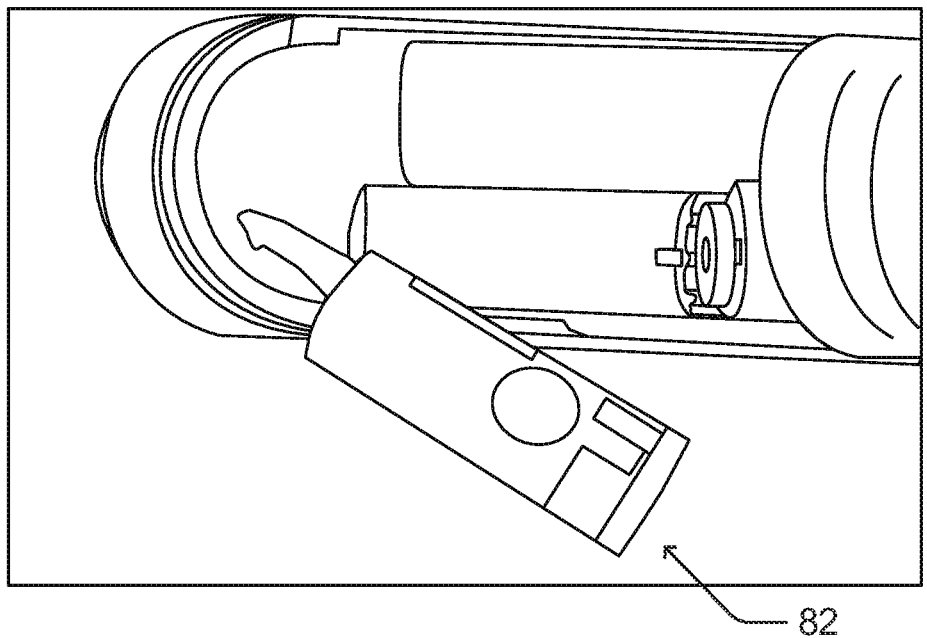
FIG. 6A is a top view of the front part of the skin treatment device as shown in FIG. 2, but with the cartridge in a position which in some embodiments is a preliminary position for inserting the cartridge to the device.
Figure 6B:
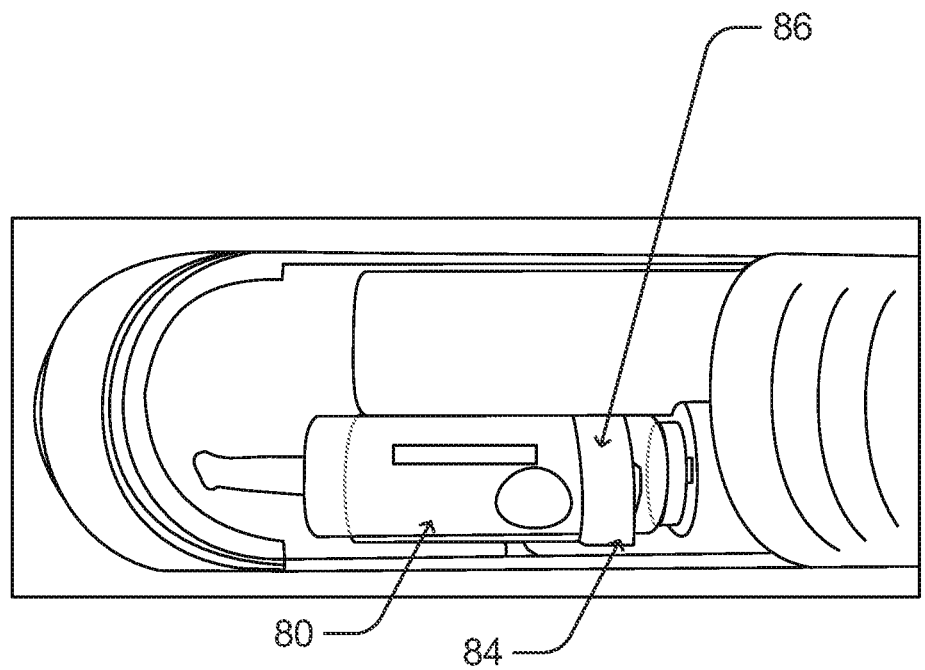
FIG. 6B is a top view of the front part of the skin treatment device as shown in FIG. 2, but with the cartridge secured position in the device.

The cartridge 40 shown in FIGS. 6A and 6B also includes a tag 84 (indicated in FIG. 6B) at its distal end 59. The tag 84 enables gripping of the cartridge to pull it from the secured position 80. The tag 84 is in the illustrated embodiment formed from a flexible plastic sheet 86 that is wrapped around the distal end 59 of the barrel 46. In other embodiments other gripping members may be included on the cartridge 40 instead of or in addition to tag 84. However, in some embodiments the gripping member in any case protrudes from a part of the barrel 46.

Figure 7:
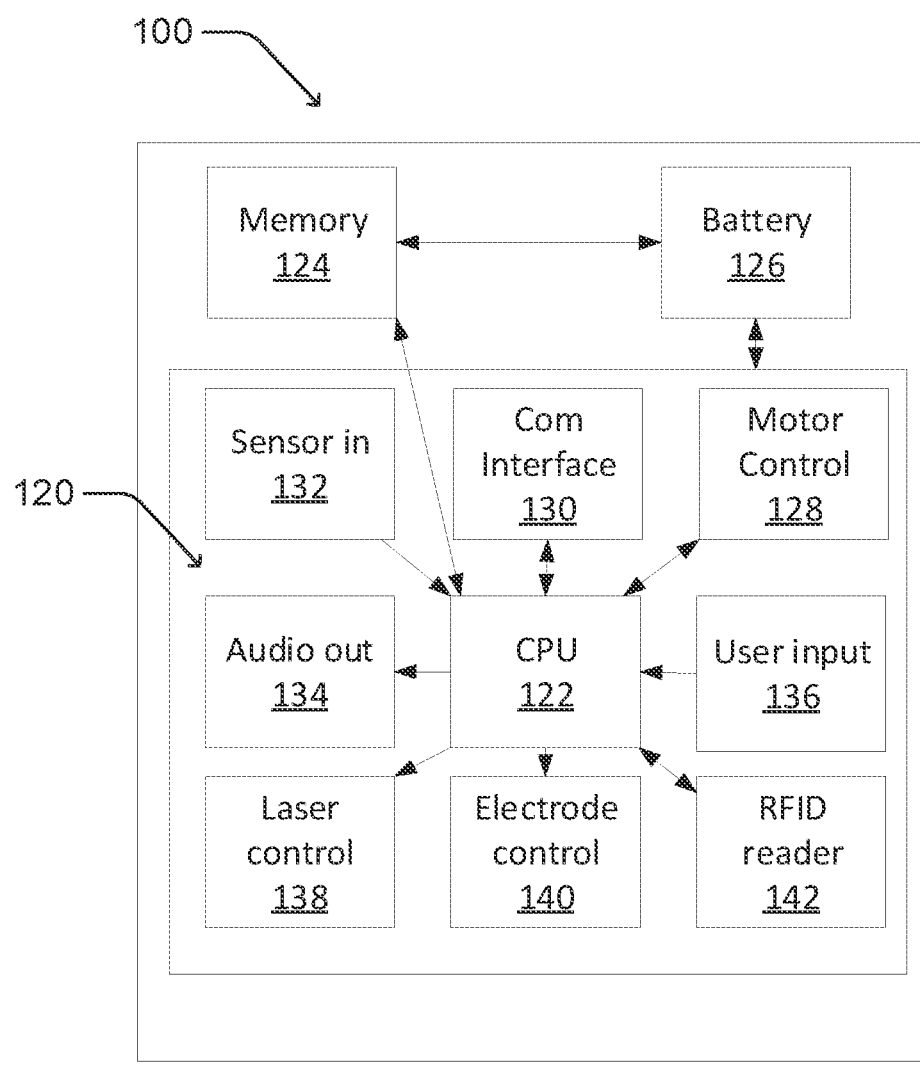
FIG. 7 is a conceptual block diagram showing the principal electronic components for controlling a device in accordance one or more aspects of the present invention.

As will be understood from the above description the design of the cartridge and the skin treatment device may advantageously provide for removal and/or replacement of a fluid dispenser in an easy and/or reliable and/or quick manner, FIG. 7 shows a conceptual block 100 diagram of electronic and components of an exemplary device that may be used for or with one or more aspects of the present invention. The device includes a processing system 120, which may be comprised of one or more processing chips. The processing system 120 includes one or more microprocessors, microcontrollers, ASIC chips and the like, and may include a memory. Additionally or alternatively it may interface with a separate memory 124. The memory 124 comprises one or more machine readable storage devices which store instructions and/or data for controlling operation of the processing system 120. In this instance, memory system 124 includes a system memory (e.g. a ROM for a Bios), volatile memory (e.g. a random access memory such as one or more DRAM modules) and non-volatile memory (e.g. Flash memory or other EEPROM device). The device is also powered by a battery 126 held within the body 12 of the device.

In the illustrated example in FIG. 7, the processing system has a Central Processing Unit (CPU) 122 and several peripheral components 128-142. The peripheral components include motor control component 128; a wireless communication interface 130, e.g. Bluetooth, Wi-Fi, 3G, LTE, and the like; processing component 132 for receiving measurements from sensors, such as a thermistor; processing component 134 for delivering an audio output (e.g. to a speaker on in the device); a user input control component 136 for receiving user controls such as actuation of button 16; a laser control component 138; electrode control component 140; and an RFID reader component 142. It will be appreciated that one or more of the peripheral components may be, or include, analog components.

In some embodiments, the cartridge 40 also includes a passive RFID tag 88, as shown in FIG. 3A. The RFID tag may, for example, adhesively wrap around a part of the barrel 46. The RFID tag, operating with the RFID reader 142 in the device 10, may be used for a variety of different functions. For example, the processing system 120 may be configured to verify that the cartridge is from an authorized source by comparing an identification (ID) number read from the tag against a database of approved ID numbers. The tag may also be used to indicate the type of the fluid in the cartridge, for example a fluid (e.g. a glycerin based fluid) for RF treatment or a fluid (e.g. a hyaluronic acid based fluid) for electroporation treatment. Upon determining the type of fluid/treatment, the processing system 120 operates the motor according to a program that is specific to the determined type. In some embodiments, the processing system 120, operating the program, is configured to provide an indication to the user to instruct the user when to move treatment to a different part of the person's body, based on the processing system 120 knowing the amount of fluid left in the single use cartridge. For example, the device may provide an audible alert when half of the fluid has used to indicate that the person should move the device from a left side of their face to the right side or vice-versa.

Further, the processing system 120 may be configured to use RDIF to facilitate enforcement of one-time use (i.e. single use) of each cartridge. For example, once the ID has been read and some predefined condition that indicates a completion of a single use is met, then the processing system 120 will not permit operation of the motor until a cartridge with a new ID is placed in the device. The predefined condition may be, for example, that a treatment program with the ID has been completed; that the cartridge with the read ID has been removed from the device; that a predefined amount of time has passed since a treatment program for the ID was started or paused; or that a treatment program for the ID was started and the device was subsequently turned off.

As will be appreciated, the use of the RFID may involve interaction with a remote database so part of the processing system used to implement the present invention may be distributed to include the processing system 120 in the device and a remote processing system accessed using communication interface 130. Having a distributed processing system may likewise be employed for various other aspects of the disclosure, as will be appreciated by a person skilled in the art.

Where a given item is referenced herein with the preposition "a" or "an", it is not intended to exclude the possibility of additional instances of such an item, unless context requires otherwise.

Where the specification defines a range, the stated outer extremities of the range are part of the range, unless context requires exclusion of the outer extremities from the range. From example, a range defined in terms of being between X and Y or from X to Y, should be interpreted as including X and Y.

The invention disclosed and defined herein extends to all plausible combinations of two or more of the individual features mentioned or evident from the text or drawings. All of these different combinations constitute various alternative aspects of the invention.

What is claimed is:

1. A handheld skin treatment device configured to deliver fluid and any of: a) an electromagnetic energy b) an electrical energy and c) both the electromagnetic energy and the electrical energy to a person's skin via a surface region on the device, the device comprising:
a device body comprising:
a head comprising the surface region; and
a cartridge containment portion comprising a container holding portion, and a path through the head, the path having a distal end, the distal end having an opening within the surface region;
wherein the cartridge containment portion has a locating feature; and
a replaceable fluid cartridge secured in the cartridge containment portion and having a rigid cartridge body that includes a spout extending through the path,
wherein the locating feature positions a tip of the spout at the opening;
wherein the locating feature comprises a stop in the distal end of the path, wherein the spout has a distal end abutting the stop to position the tip of the spout at the opening.

2. The skin treatment device according to claim 1, wherein the locating feature positions the tip beneath a distal part of the surface region such that the tip does not protrude from the head.

3. The skin treatment device according to claim 1, wherein the stop is provided by an inward tapering of the path in the distal end of the path.

4. The skin treatment device according to claim 1, wherein the stop seals against the distal end of the spout.

5. The skin treatment device according to claim 1, wherein the stop abuts the distal end of the spout by abutting the tip of the spout.

6. The skin treatment device according to claim 1, wherein the spout is elongate and includes a bend.

7. The skin treatment device according to claim 1, wherein a wall of the path has a bend, but the path is shaped to include a line of sight through a channel.

8. The skin treatment device according to claim 1, wherein the head includes:
a plurality of electrodes wherein the device is configurable to selectively deliver the electrical energy and wherein the electrical energy comprises radiofrequency (RF) or electroporation treatment energy; and
one or more light sources for delivering low-level laser light therapy (LLLT) treatment energy,
wherein the one or more lights sources are positioned to emit light from within a region surrounded by the plurality of electrodes.

9. The skin treatment device according to claim 1, wherein the path comprises an elongate channel.

10. The skin treatment device according to claim 8, wherein said opening in the surface region is an opening in a part having an appearance as one of said plurality of electrodes.

11. The skin treatment device according to claim 1, wherein a wall of the device body is displaceable to expose the container holding portion to allow the cartridge to be replaced, wherein at least during replacement the head is fixedly connected to a portion of the body that includes the container holding portion.

12. The skin treatment device according to claim 1, wherein the device is configured to output an indication to a user indicating that the device should be moved from one side of a face of the person to another side of the face.

13. The skin treatment device according to claim 1, wherein the spout is integrally formed with the rigid cartridge body.

14. A handheld skin treatment device configured to deliver fluid and any of: a) an electromagnetic energy b) an electrical energy and c) both the electromagnetic energy and the electrical energy to a person's skin via a surface region on the device, the device comprising:
- a device body comprising:
  - a head comprising the surface region; and
  - a cartridge containment portion comprising a container holding portion, and a path through the head, the path having a distal end, the distal end having an opening within the surface region;
  - wherein the cartridge containment portion has a locating feature; a replaceable fluid cartridge secured in the cartridge containment portion and having a rigid cartridge body that includes a spout extending through the path, wherein the locating feature positions a tip of the spout at the opening wherein the device body further comprises:
- at least one sensor for sensing an identification on the replaceable fluid cartridge;
- a motor for driving an actuator against the replaceable fluid cartridge to eject fluid from the replaceable fluid cartridge via the opening; and
- a processing system configured to:
  - detect the identification using the at least sensor;
  - drive delivery of any of: the electromagnetic energy, the electrical energy and both the electromagnetic energy and the electrical energy according to a selected one of a plurality of energy types; and
  - based at least in part on the detected identification, control the motor in manner tailored to said selected one of the plurality of energy types.

15. A handheld skin treatment device configured to deliver fluid and at least any of: a) an electromagnetic energy b) an electrical energy and c) both the electromagnetic energy and the electrical energy to a person's skin via a surface region on the device, the device comprising:
- a device body comprising:
  - a head comprising the surface region;
  - a cartridge containment portion comprising a container holding portion, and a path through the head, the path having a distal end, the distal end having an opening within the surface region;
- a replaceable fluid cartridge secured in the cartridge containment portion and having a rigid cartridge body that includes a spout extending through the path; and
- a processing system configured to limit a motor to execute a fluid ejection procedure only once for the replaceable fluid cartridge;
- wherein the cartridge containment portion has a locating feature;
- wherein the locating feature positions a tip of the spout at the opening.

* * * * *